(12) United States Patent
Chaniotakis et al.

(10) Patent No.: US 8,454,509 B1
(45) Date of Patent: Jun. 4, 2013

(54) NANOSTRUCTURED COMPOSITE MATERIAL AND BIOSENSOR COMPRISING IT

(75) Inventors: Nikolaos Chaniotakis, Crete (GR); Achilleas Tsoukalis, Attiki (GR); Maria Chatzimarinaki, Crete (GR); Vassiliki Vamvakaki, Crete (GR); Vassiliki Stavgianoudaki, Crete (GR)

(73) Assignee: Achilleas Tsoukalis, Attiki (GR)

( * ) Notice: Subject to any disclaimer, the term of this patent is extended or adjusted under 35 U.S.C. 154(b) by 1020 days.

(21) Appl. No.: 12/487,741

(22) Filed: Jun. 19, 2009

(30) Foreign Application Priority Data

Jun. 20, 2008 (GR) .................................. 080100409

(51) Int. Cl.
*A61B 5/00* (2006.01)
*C08K 5/17* (2006.01)

(52) U.S. Cl.
USPC ......................................... 600/309; 524/249

(58) Field of Classification Search
USPC .......................................... 524/249; 600/309
See application file for complete search history.

(56) References Cited

U.S. PATENT DOCUMENTS

2005/0011827 A1    1/2005   Koslow

OTHER PUBLICATIONS

Patwardhan et al. Bioinspired Synthesis of New Silica Structures. Chem. Commun., 2003, 1122-1123.*

Wu, et al., "Amperometric Glucose Sensor Based on Catalytic Reduction of Dissolved Oxygen at Soluble Carbon Nanofiber" Biosensors and Bioelectronics, Elsevier BV, N L, vol. 23, No. 4, Oct. 17, 2007, pp. 479-484, XP022302117.
Vamvakaki, et al., "Carbon Nanofiber-Based Glucose Biosensor" Analytical Chemistry, Aug. 1, 2006, vol. 78, No. 15, pp. 5538-5542, XP002544824.
Toebes, et al., "The Influence of Oxydation on the Texture and The Number of Oxygen-Containing Surface Groups of Carbon Nanofibers" Carbon, vol. 42, 2004, pp. 307-315, XP002544825.
Rasheed, et al., "The Efficiency of the Oxydation of Carbon Nanofibers With Various Oxidizing Agents" Carbon, vol. 45, 2007, pp. 1072-1080, XP002544826.
Vamvakaki, et al., "Biomimetically Synthesized Silica-Carbon Nanofiber Architectures for The Development of Highly Stable Electrochemical Biosensor Systems", Analytical Chemistry, Aug. 1, 2008, vol. 80, No. 15, pp. 5970-5975, XP002544827.
Patel, et al., "In Situ Encapsulation of Horseradish Peroxidase in Electrospun Porous Silica Fibers for Potential Biosensor Applications", Nano Letters, American Chemical Society, vol. 6, No. 5, pp. 1042-1046 (2006).
European Patent Office, "Extended European Search Report"; issued in EP Patent Application No. 09 16 2952.7, on Sep. 21, 2009; pp. 1-5.
European Patent Office, "Official Communication dated Oct. 26, 2011" in EP Patent Application No. 09 162 952.7; pp. 1-4.

* cited by examiner

*Primary Examiner* — John Uselding
(74) *Attorney, Agent, or Firm* — Duane Morris LLP; J. Rodman Steele, Jr.; Gregory M. Lefkowitz (57) ABSTRACT

A nanostructured composite is provided which comprises a matrix comprising carbon nanofibers, and a biochemical receptor, especially an enzyme, immobilized in the matrix, where the carbon nanofibers have been subject to an oxidation treatment. In a preferred embodiment, the nanostructured composite further comprises a biomimetically synthesized silica matrix.

15 Claims, 6 Drawing Sheets

NANOSTRUCTURED COMPOSITE MATERIAL AND BIOSENSOR COMPRISING IT

CROSS-REFERENCE TO RELATED APPLICATION

This application claims the benefit of Greek Patent Application 20080100409, filed on Jun. 20, 2008, which is hereby incorporated by reference.

BACKGROUND OF THE INVENTION

The present invention relates to nanostructured composite materials which are suitable for the application in biosensors, and to biosensors comprising those nanostructured composite materials.

A nanostructured composite material (nanocomposite) is a composite material in which at least one of the phases has at least one dimension which is of the order of nanometers.

A biosensor is a device that uses specific biochemical reactions mediated by a receptor selected from the group consisting of isolated enzymes, microorganisms, immunosystems, tissues, organelles, whole cells, antibodies, nucleic acids and combinations thereof to detect chemical compounds (analytes) usually by means of electrical, thermal or optical signals. Within the biosensor, the receptor is coupled to a transducer by means of immobilization.

DESCRIBED OF THE PRIOR ART

It has been suggested to immobilize the biochemical receptor on a matrix formed of a nanostructured carbon material like carbon nanotubes or carbon nanofibers (See, e.g. Vamvakaki, V; Tsageraki, K. and Chaniotakis, N: Anal. Chem. 2006, 78, 5538-5542). Within a biosensor generating electrical signals, nanostructured carbon materials can fulfill a dual function i.e. they provide a matrix for the immobilization of the receptor and at the same time act as a transducer for the electrical signal generated by the biochemical reaction. Thus, immobilization of the biochemical receptor on a nanostructured matrix formed of a carbon material allows for a direct electron transfer from the receptor to the immobilization surface.

The use of carbon nanotubes in biosensors is limited by the fact that the tubular nanotubes have closed shells which do not allow for a high degree of functionalization. This is because adsorption or covalent immobilization of a receptor can be achieved only at the functionalized ends of the opened nanotubes. For this reason, the amount of biochemical receptors, e.g. enzymes that can be immobilized on carbon nanotubes is limited, resulting in receptor-matrix composites with sensitivities and stability properties that are not fully optimized.

On the other hand, carbon nanofibers, due to their more open surface structure, are expected to have a much larger functionalizable surface area. Carbon nanofibers are cylindrical nanostructures comprising graphene layers arranged as stacked cones, cups, or plates. Thus, for carbon nanofibers a significantly higher ratio of the number of surface-active groups to the volume can be expected compared to that of the glassy-like surface of the carbon nanotubes. Additionally, nanofibers have a higher conductivity than nanotubes of prior art, thus giving larger signals to the underlying electrode surface (e.g. a metal wire) or semiconductor substrate (in case of an integrated multi bio-sensor ChemFet plate), resulting in a better signal to noise ratio, i.e. providing more accurate and faster filtered results. However, carbon nanofibers exhibit a remarkable hydrophobicity which is detrimental to the adsorption of biochemical receptors.

SUMMARY OF THE INVENTION

The present invention provides a nanostructured composite material comprising a matrix comprising carbon nanofibers, and a biochemical receptor, especially an enzyme, immobilized in the matrix comprising carbon nanofibers wherein the carbon nanofibers have an increased amount of functional surface groups, especially acidic functional groups, resulting in a more hydrophilic character, thus providing for a reliable and durable immobilization of a large number of receptor units.

The amount of surface functional groups can be increased by subjecting the carbon nanofibers to an activation process comprising treatment of the carbon nanofibers with oxidizing agents before immobilization of the biochemical receptor thereon.

Accordingly, the nanostructured composite material of the present invention comprises a matrix comprising carbon nanofibers, and a biochemical receptor, especially an enzyme, immobilized in the matrix comprising carbon nanofibers, characterized in that the carbon nanofibers are activated, i.e. have been subject to an oxidation treatment. Carbon materials which have been subject to an activation treatment are characterized by a developed surface area, formation of shallow and tiny pores and an increased number of oxygen-containing surface functional groups, especially acidic functional groups. Accordingly the hydrophilic character of the surface of the carbon nanofibers is increased. Thus activated carbon nanofibers provide a very large number of adsorption sites, and can thus immobilize an increased amount of biochemical receptor units.

Accordingly, the nanostructured composite material of the present invention is obtained by a method comprising the steps of activation of carbon nanofibers by treatment with an oxidizing agent, adjustment of the pH value at the surface of the carbon nanofibers to 7 and immobilization of a biochemical receptor on the activated carbon nanofibers.

BRIEF DESCRIPTION OF THE DRAWING

In the following, the present invention will be described in greater detail with reference to the accompanying figures, in which.

DESCRIPTION OF THE PREFERRED EMBODIMENTS

In the nanostructured composite materials of the present invention, grahitized as well as non-graphitized carbon nanofibers or mixtures thereof can be used.

Activation is carried out by applying a suitable oxidizing agent and optional supply of additional thermal energy and/or irradiation, e.g. UV irradiation. In a preferred method, concentrated hydrogen peroxide is used as the oxidation agent. Alternatively, activation can be carried out by treating the carbon nanofibres with concentrated nitric acid or a mixture of concentrated nitric and sulphuric acid, preferably under ultrasonification. Further alternatively, activation can be carried out by exposing the carbon nanofibers to oxygen or any other suitable oxidation agent, e.g. potassium permanganate ($KMnO_4$) or ruthenium tetroxide ($RuO_4$), preferably at elevated temperature.

It is important that after the activation treatment neutralization of the pH at the surface of the activated carbon nanofibers is performed. Neutralization of the pH value ensures that the activity of the enzyme or other biochemical receptor which is to be immobilized on the oxidized carbon nanofibers will remain intact and will not be damaged due to very low or very high pH values.

As a result of the activation procedure, the number of surface functional groups, especially the number of acidic surface functional groups, increases at least by a factor of three. Preferably, the amount of acidic surface functional groups in the activated carbon nanofibers is at least $6*10^{-5}$ mol/g, as determined by direct titration with a solution of 0.01 mol/l sodium hydroxide. Higher amounts of surface functional groups can be achieved, depending on the selected oxidation agent and the duration of the oxidation treatment. Typical acidic surface functional groups are carboxyl, lactone, and phenol groups. When hydrogen peroxide or a mixture of concentrated nitric and sulphuric acid are used as the oxidation agent, the amount of carboxylic groups as determined by titration with a 0.01 mol/l solution of sodium hydrogen carbonate is at least about a fourth of the overall number of acidic surface functional groups. However, the fractions of the different types of acidic functional groups depend on the selected oxidation agent(s) and the duration of the oxidation treatment.

The fibrous structure of the carbon nanofibers is retained after the oxidation treatment. The carbon nanofibers usually form an entangled, spaghetti-like network. Typically, the oxidized nanofibers have a mean diameter of 60 to 200 nm while their length is in the order of tens of micrometers (usually >20 μm).

The nanostructured composite material of the invention is obtained by immobilization of a biochemical receptor in a matrix comprising carbon nanofibers. Any biochemical receptor capable of generating a signal which can be transduced by carbon nanofibers can be applied. Preferably, the biochemical receptor is a receptor which is involved into an electrochemical reaction (redox reaction) with the analyte, thus generating an electrical signal which is transduced by the activated carbon nanofibers. The biochemical receptor is selected from the group consisting of isolated enzymes, microorganisms, immunosystems, tissues, organelles, whole cells, antibodies, nucleic acids and combinations thereof. Preferably, enzymes are used as receptors because the reaction of an enzyme with an analyte is highly specific.

Due to the activation treatment preceding the immobilization of the receptor, both the porosity and the hydrophilicity of the surface of the carbon nanofibers has increased. The more developed surface might enable deeper penetration of a biochemical receptor like an enzyme into the spaghetti like nanofiber structure, while the presence of an increased amount of surface functional groups facilitates adsorption of an increased amount of receptor units, and stronger electrostatic adhesion thereof. Thus the amount of the immobilized biochemical receptor units and the stability thereof is increased as a result of the oxidation treatment of the carbon nanofibers.

In a preferred embodiment, the receptor comprises the enzyme glucose oxidase (GOx). A nanostructured composite comprising a matrix comprising activated carbon nanofibers and a biochemical receptor comprising the enzyme glucose oxidase immobilized in said matrix is suitable for application in a biosensor for continuous monitoring of glucose. Such devices are needed for diabetes care.

Upon immobilization of the biochemical receptor in a matrix comprising activated carbon nanofibers, deep penetration of the receptor into the matrix structure is facilitated by ultrasonic treatment.

Even though adsorption or covalent immobilization of the biochemical receptor onto the surface of carbon nanofibers which have been subject to an oxidation treatment provides a significant stabilization effect, this is not sufficient for long-term implantable biosensor systems. Since enzymes and other biochemical receptors are not very stable outside their biological environment, they are prone to denaturation or inactivation by even very small changes in pH, temperature, or the presence of traces of organic solvents and detergents usually employed for the construction of a biosensor. Another very important factor drastically influencing the biosensor stability is the presence of proteases, which are found in virtually any analyte solution. Finally, leaching of the receptor away from the matrix is another problem, causing signal drift, and decreasing the biosensor sensitivity over time. All these parameters have a detrimental effect on the analytical characteristics of the biosensor, decreasing both the operational and storage stabilities of biosensors, effects that are very profound when these biosensors are applied in harsh environments, or in-vivo.

Therefore, in a preferred embodiment of the present invention, the nanostructured composite is further stabilized by deposition of a biomimetically synthesized silica matrix onto the activated carbon nanofibres with the receptor immobilized thereon.

The term "biomimetic" refers to a laboratory procedure designed to imitate a natural chemical process and to a compound that mimics a biological material in its structure and/or function.

In biomimetic synthesis, after immobilization of the biochemical receptor, a scaffold comprising of a protein or a polymer is deposited as an intermediate layer onto the surface of the nanostructured composite, which directs growth of a matrix comprising silica precipitated from a precursor solution. The silica matrix is mainly formed of a network of fused silica particles.

Methods for the biomimetic synthesis of silica are known in the art, see e.g. Siddharth V. Patwardhan, Stephen J. Clarson and Carole C. Perrya: On the role(s) of additives in bioinspired silicification Chem. Commun., 2005, 1113-1121. In this document, a plurality of suitable scaffold-forming proteins and polymers are listed, which can be used in the method of production of a nanostructured composite material according to the present invention. Examples of suitable scaffold forming materials are e.g. poly-L-lysine, polyethylenimine, polyallyamine, cellulose, R5 peptide, poly-L-arginine, poly-L histidine, lysine oligomers, poly(allylamine hydrochloride).

Accordingly, a method for producing a nanostructured composite material according to the preferred embodiment described above comprises the steps of activation of the carbon nanofibers by treatment with an oxidizing agent, adjustment of the pH value at the surface of the carbon nanofibers to 7, immobilization of a biochemical receptor on the activated carbon nanofibers, deposition of a scaffold comprising a protein or polymer onto the carbon nanofibers and precipitation of a silica matrix onto the scaffold.

Figure 1:
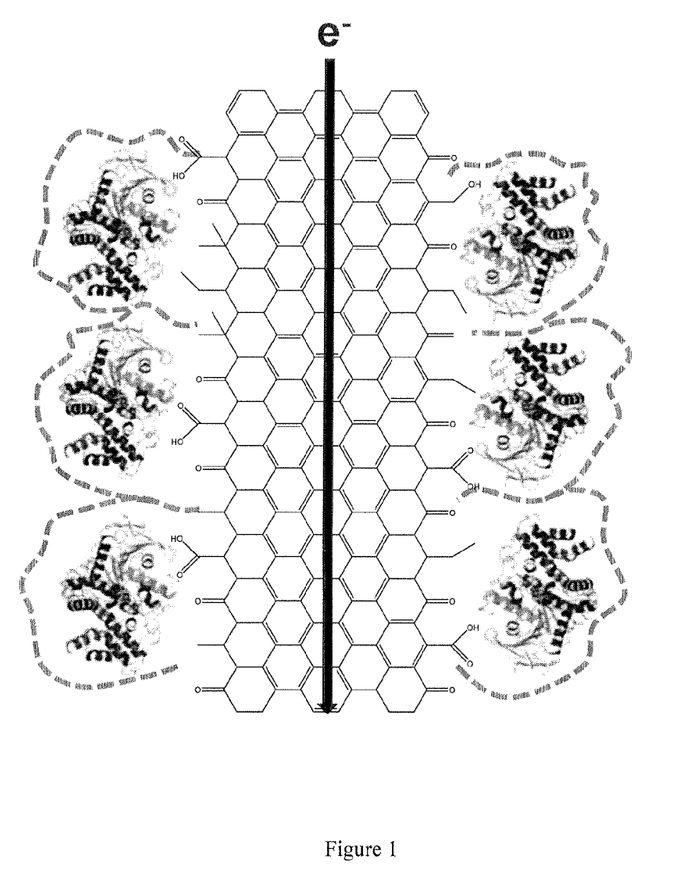
FIG. 1 shows a schematic representation of a nanostructured composite material according to a specific embodiment of the present invention.
Figure 2:
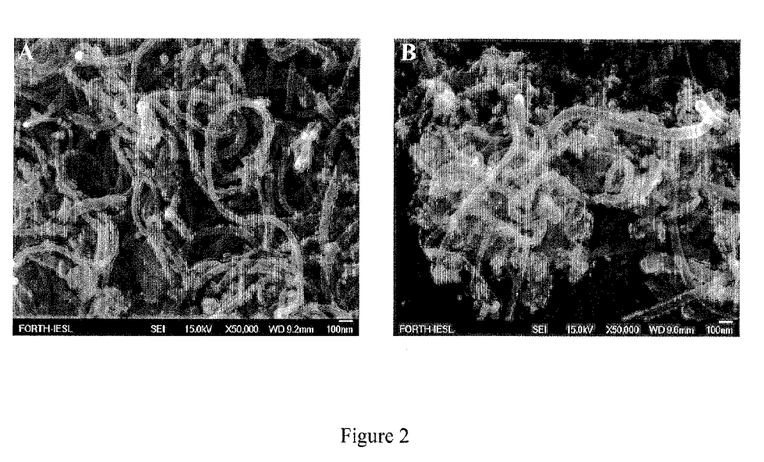
FIG. 2 shows SEM images of A) carbon nanofibers, B) carbon nanofibers with a biomimetically synthesized silica matrix thereon.

A schematic representation of a nanostructured composite comprising oxidized carbon nanofibers, a biochemical receptor immobilized thereon and a silica matrix precipitate on a scaffold comprising a polymer or a peptide is shown in FIG. 1. Receptor molecules are attached to the functional groups at the surface of a carbon nanofiber strand. The composite formed of oxidized carbon nanofibers and the biochemical receptor immobilized thereon is encapsulated by a matrix comprising biomimetically synthesized silica (represented by dashed lines) on a scaffold comprising a polymer or a protein. The carbon nanofiber strand provides electrical contact to the surface of a working electrode, which is connected to electronics for signal conditioning and display. The oxidized carbon nanofibers facilitate the immobilization and first stabilization of the receptor, while the silica matrix acts as an encapsulating protection layer. Thus the oxidized carbon nanofibers in combination with the biomimetically synthesized silica matrix provide ideal architectures for the design and development of highly stable biosensor systems.

Furthermore, since the silica protective layer itself is substantially free of receptor, the substrate (analyte) can freely penetrate through the pores in the silica layer, eliminating the diffusion of other redox interfering species, as well as cells and large proteins. Due to the immobilization of the receptor directly on the oxidized carbon nanofibres a direct electron transfer between the receptor and the carbon nanofiber transducer is achieved, mediating the signal very efficiently to the electronics. Thus fast kinetics are obtained, free from interference and signal drifts, with increased receptor stabilization over time, resulting in a better performing biosensor with accuracy and stability over an increased time and against chemical "noise" substances, so that it can according to our measurements be used in-vivo and in a closed loop infusion setup The silica matrix must be thick enough for sufficient protection, but thin enough in order to allow for the substrate (glucose in the case of a receptor comprising Glucose Oxidase) to reach the active center of the receptor. The pores must also be small enough not to allow for any proteases to reach the receptor. Based on TEM images, the thickness of this silica matrix ranges between 0.5 and 100 nm. The porosity is controlled by the thickness of the silica. The thicker the silica matrix the lower is the porosity.

In a further preferred embodiment, porin molecules or synthetic nanoporous materials are incorporated into the silica matrix of the nanostructured composite material. Porins are beta barrel proteins that cross a cellular membrane and act as a pore through which molecules can diffuse. Unlike other membrane transport proteins, porins are large enough to allow passive diffusion—i.e., they act as channels that are specific to different types of molecules. They are present in the outer membrane of Gram-negative bacteria, the mitochondria, and the chloroplast. Porins incorporated into the silica matrix behave like selective channels since only molecules of small diameter can freely diffuse into the interior of the composite and reach the biochemical receptor immobilized on the oxidized carbon nanofibers while large molecules like proteases cannot pass the channel so that they do not reach the receptor.

The present invention is further directed to biosensors, especially electrochemical biosensors, comprising the nanostructured composite described herein above.

An electrochemical biosensor can be constructed either as a two electrode sensor or as a three electrode sensor. A two electrode sensor comprises a working electrode, preferably made of platinum in contact with the nanostructured composite material described herein above, and a reference electrode preferably a Ag/AgCl electrode, in direct contact with analyte or living tissue. In a three-electrode sensor a third electrode, preferably made of platinum, too, is located in close proximity to the working electrode. The nanostructured composite material may be deposited, precipitated or coated onto the working electrode, thus forming a layer on the surface of the working electrode. These methods are known in the art and well established. For instance, the electrode surface can be pretreated mechanically by a roughening treatment (e.g. by grit-blasting) and/or chemically (e.g. by etching) in order to facilitate adherence of the carbon nanofibres.

The related electronics and housing of biosensors is known in the art and therefore does not need to be described here in detail.

In a preferred embodiment, the biosensor is a single needle biosensor which is implantable for a subcutaneous measurement lasting several days as long as such needle can be accepted without fear of contamination, usually a week.

A further preferred embodiment comprises a plurality of biosensors (multi-biosensor device) with at least one of the biosensors comprising the nanostructured composite described herein above. For instance the device is formed of a plate comprising several islands of biosensors. An exemplary application is an implantable pump comprising a plurality of biosensors on the surface thereof.

In a preferred multi-biosensor device, each biosensor is adapted to be individually activated, i.e. means are provided to achieve individual activation of each individual biosensor. This activation can be achieved by removing a protective covering layer from the individual sensor to be activated and electronic activation of the uncovered sensor. Preferably, the removable covering layer is substantially impermeable to fluid, since contact with body fluids might degrade the biochemical receptor of the sensor even when the sensor is not electronically activated yet. For instance, activation of individual biosensors can be initiated by a process triggered electrically (i.e. by application of an electric current or potential), like electroerosion. Therefore, in a preferred embodiment the biosensors are provided with a covering layer comprising an electrically erodible polymer which is substantially impermeable to fluids, and means are provided to achieve sequential activation of the individual biosensors by electroerosion of said electrically erodible polymer and electronic activation of the uncovered sensor. Suitable removable polymers are known in the art, see, e.g. Kwon et al., "Electrically erodible polymer gel for controlled release of drugs", Nature, 354: 291-93 (1991).

Sequential activation of the biosensors (one after the other) allows for significant increase of the time the device is capable of providing accurate measurement results, compared to a device comprising a single biosensor only. Since the multi-sensor device comprises a plurality of biosensors, in the case that the active biosensor appears to cease working accurately, one of the other biosensors can be activated and take over from the one being activate so far.

Preferably the biosensor or the multi-biosensor device is implantable into a being, especially a human being. Immobilization of the receptor into the matrix comprising activated carbon nanofibers, and the additional protection provided by the biomimetically synthesized silica matrix and/or a removable substantially impermeable covering layer as described above and/or a further coating comprising a biocompatible material (see below) ensure stability of the receptor over a long period of time even in the implanted state. Thus the accuracy of the biosensor is not deteriorated when implanted in a living being. Preferably, the biosensors or multi-biosensor devices are implantable by means of minimal invasive technique. In a preferred embodiment, the multi-biosensor device can be implanted subcutaneously.

In a further preferred embodiment the biocompatibility of the biosensor or the multi-biosensor device is improved by providing a layer comprising a biocompatible material on at least a part of the surface of the biosensor of the multi-biosensor device. Preferably the layer comprises a biocompatible polymer or a combination of different biocompatible polymers. A suitable biocompatible polymer material is polyxylene. Other suitable materials are sulfonated polytetrafluoroethylene, polytetrafluoroethylene, preferably expanded polytetrafluoroethylene, polyester, porous silicone, hydrophilic polyvinylidene fluoride, mixed cellulose esters, polyvinyl chloride, polypropylene, polyethylene, polysulfone, polyethersulfone, cellulose acetate, nylon, polycarbonate, and polymethylmethacrylate. The biocompatible layer facilitates attachment of the device to the fibrous tissue build up in response of the organism to the introduction of a foreign material. Thus the biocompatible layer acts an angiogenic layer i.e. it promotes and maintains the formation and healing of blood microcirculation capillaries around the implanted device, thus maintaining the blood circulation in the proximity of the implanted device and providing realistic amounts of the analyte. The angiogenic layer is porous so that the newly growing tissue penetrates into the angiogenic material, thus interlocking with the implanted sensor device. In the region proximate to the electrodes (e.g. around the tip of a needle-type sensor), the biocompatible layer may be designed as a composite angiogenic and filtration layer, i.e. as a multifunctional layer. The filtration layer controls access to the receptor, i.e. it allows passing of the analyte, but keeps out proteases, tissue macrophages and any other species which could destabilize or degrade the enzyme or other receptor immobilized on the carbon nanofibers. Thus in addition to the silica matrix, further protection of the receptor is achieved. Layers of different materials can be combined to achieve the combination of multiple functions like angiogenese and filtration. According to their related functions in the multi-layer composite, the angiogenic layer is oriented outwards from the sensor, while the semipermeable filtration layer is oriented towards the interior of the sensor device. Preferably, the semipermeable filtration layer has smaller pores than the angiogenic layer. Suitable materials for the filtration layer are polyurethane, polypropylene, polysulfone, polytetrafluoroethylene and polyethylene terephtalate. The filtration layer itself can be a combination of layers different in composition and/or porosity.

Thus, in a preferred embodiment of an implantable sensor device or multisensory device, e.g. an implantable pump comprising a plurality of biosensors on the surface thereof, the outermost (external) surface of the device comprises an angiogenic layer as described above, optionally with removable impermeable coverings provided on the individual sensor islands beneath the outer angiogenic layer. Thus starting from the working electrode as the innermost part, the sensor device might comprise the following layer sequence: (i) metallic surface of the working electrode, (ii) matrix comprising oxidized carbon nanofibers with the receptor immobilized therein, (iii) optionally a biomimetically synthesized silica matrix as described above, (iv) optionally a removable cover layer which is non-permeable to fluids and which is removed when the activation of the sensor is initiated as described above, (v) optionally an angiogenic layer, which might also cover the whole or parts of the surface of the housing.

In a preferred embodiment, the receptor of the biosensor comprises the enzyme glucose oxidase (GOx). Thus the biosensor is suitable as a continuous glucose monitoring device for diabetes care. Existing sensing devices are not enough accurate and have a drift in time, so that it was not possible so far to replace the patient's centric manual adjustment of the insulin level by an automatic algorithmic process (closed loop), although algorithms were progressing. It is also a fact that the automatic process needs a remote monitoring from professionals and large databases' knowledge in an external secondary and more "knowledgeable" algorithmic loop, and cannot be left alone in the local algorithmic process or patient's knowledge.

The improved accuracy and stability of the biosensor of the present invention permit the realization of closed loop infusion, with local algorithmic loop. A web and GSM/GPRS based telemonitoring system as described in the U.S. Pat. No. 7,161,484 B2 and in the European Patent Application EP 1 385 420 A0 (both assigned to Micrel Medical Devices S.A.) can preferably make the measurement results available for a distant physician or paramedics to validate algorithmic insulin infusion control, and distant closed loop algorithmic decisions based on large databases located in distant servers. The local loop is a short term infusion control (needed in case SGM or WiFi or WiMax transmission is impossible for some time), while the web based loop is a longer term control and validation of local loop control algorithmic parameters. An RFID type of communication between biosensor and extracorporeal analyzer is the preferred communication type.

It goes without saying that features of different preferred embodiments described herein can be combined, if desired.

EXAMPLES

Activation Treatment of Carbon Nanofibers 150 mg of carbon nanofibers (type HTE from Electrovac AG, Austria) are dispersed in 150 ml of a solution containing 30 w/w % of hydrogen peroxide. The dispersion is refluxed for two hours, while irradiated with a UV-lamp. The oxidised CNFs are rinsed with 0.01 mol/l NaOH solution and deionized water until neutral pH. The acid treated CNF are dried under vacuum at 100° C. overnight.

In another run, graphitized carbon nanofibers (type GFE from Electrovac AG, Austria) were treated with a mixture of concentrated nitric and sulphuric acid (volumic ratio 1:3) under ultrasonification.

The amount of acidic surface functional groups is determined by direct titration with a solution of 0.01 mol/l sodium hydroxide. The amount of carboxylic groups is determined by titration with a 0.01 mol/l solution of sodium hydrogen carbonate. Data obtained from carbon nanofibers with and without activation treatment are compiled in table 1:

|  | Carbon nanofibers type HTE | | Carbon nanofibers type GFE | |
| --- | --- | --- | --- | --- |
|  | original | oxidized with $H_2O_2$ | original | oxidized with $H_2SO_4/HNO_3$ |
| Acidic groups(mol/g) | $16.8 \times 10^{-6}$ | $62.4 \times 10^{-6}$ | $26.2 \times 10^{-6}$ | $345 \times 10^{-6}$ |
| COOH groups (mol/g) | — | $17.9 \times 10^{-6}$ | — | $81.4 \times 10^{-6}$ |

As a consequence of the oxidative treatment the amount of acidic surface groups has surface groups has substantially increased.

Immobilization of enzymes on oxidized carbon nanofibers.

Glucose oxidase was immobilized on oxidized carbon nanofibers (type HTE) which were prepared as described above. For comparison, in a parallel experiment glucose oxidase was immobilized on non-oxidized carbon nanofibers. Deep penetration of glucose oxidase into the matrix structure is facilitated by ultrasonic treatment.

The amount of the enzyme glucose oxidase adsorbed was found to be 14 and 18 units/g for non-oxidized and oxidized HTE carbon nanofibers respectively. Thus, due to the oxidation of the carbon nanofibers, the amount of immobilized enzyme increased by more than one third.

Preparation of nanostructured composites comprising a biomimetically silica matrix.

Figure 3:
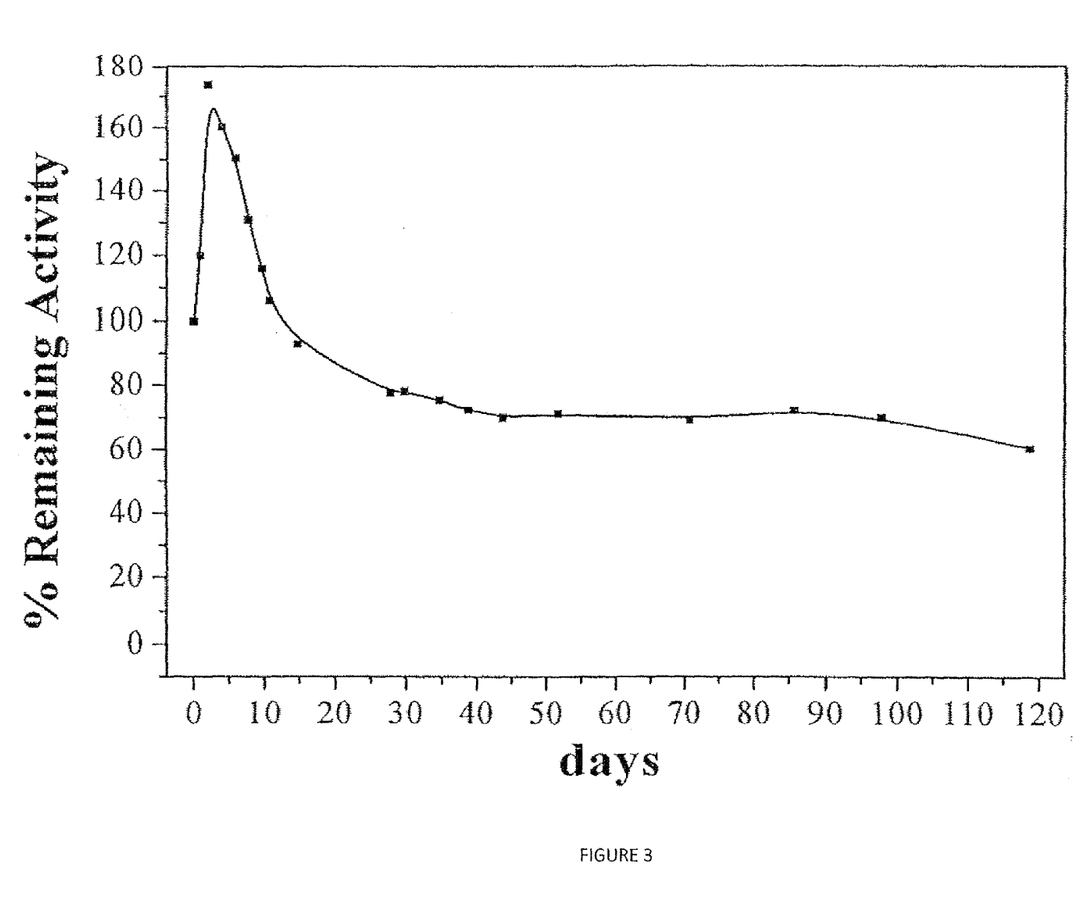
FIG. 3 displays the stability of a nanostructured composite material according to a specific embodiment of the present invention under continuous polarization (+300 mV, 25° C.)
Figure 4:
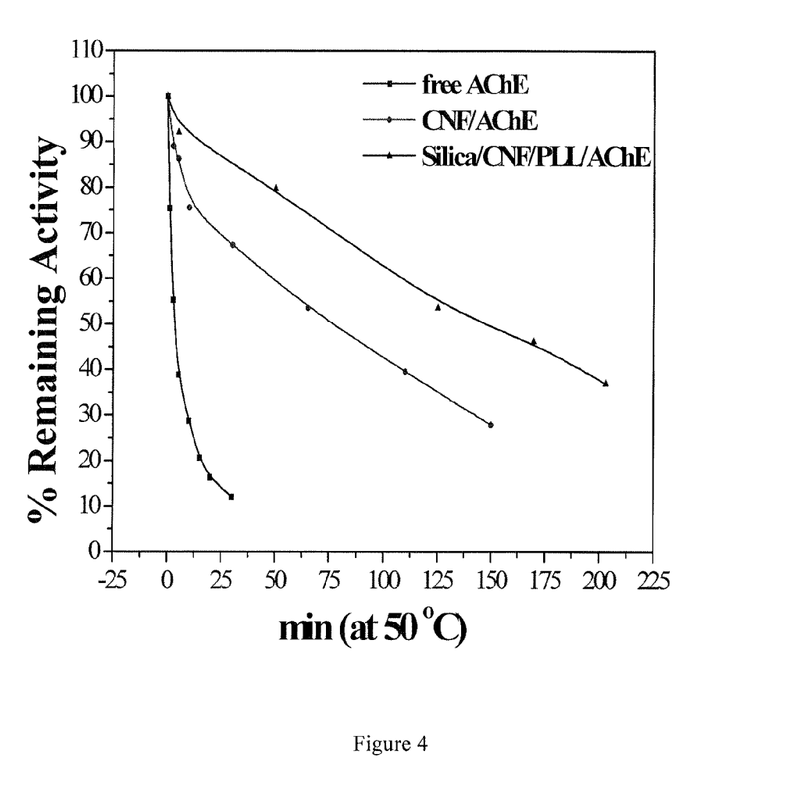
FIG. 4 shows the results of a stability study of free and immobilized AChE after incubation at 50° C.
Figure 5:
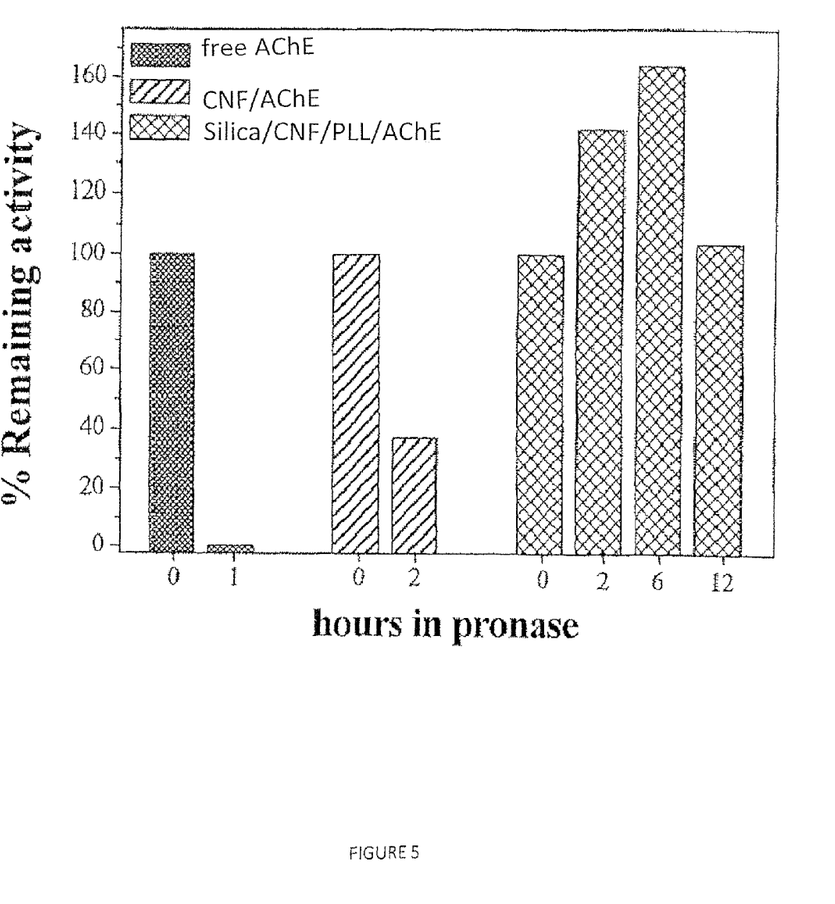
FIG. 5 shows the results of a stability study of free and immobilized AChE after incubation in protease solution (10 mg/mL)

To demonstrate the stabilizing effect of the combination of an immobilizing matrix comprising oxidized carbon nanofibers and an additional encapsulating matrix of biomimetically synthesized silica, the inherently unstable enzyme acetylcholinesterase from *Drosophila melanogaster* (Dm. AChE) is chosen as the receptor. For comparison two different nanostructured composites were studied, a first one comprising the enzyme AChE immobilized on carbon nanofibers of the type HTE (Electrovac AG, Austria) which were subjected to an oxidation treatment as described above (further referred to as CNF/AChE); and a second one comprising AChE immobilized on carbon nanofibers of the type HTE (Electrovac AG, Austria) which were subjected to an oxidation treatment as described above, and a biomimetically synthesized silica matrix (further referred to as silica/CNF/PLL/AChE).

The precipitation mixture for silica/CNF/PLL/AChE consisted of 100 μL of poly-L-lysine solution (1.0 mM in nanopure $H_2O$), 500 μL of immobilized Dm. AChE (immobilized on oxidized carbon nanofibers) phosphate solution, 300 μL of nanopure water and 100 μL of freshly prepared stock solution obtained by hydrolysis of TMOS (tetramethylorthosilicate) at a concentration of 1.0 M with 1.0 mM HCl solution. The mixture was mixed in a vortex slowly, followed by centrifugation at 4,000 rpm. The products obtained were washed twice with nanopure water. Finally, the samples obtained were dried at room temperature overnight.

SEM Studies

FIG. 2A shows the spaghetti-like network formed of carbon nanofibers. As can be seen on FIG. 2B the precipitation of the biomimetically synthesized silica matrix introduces silica particles into the cavities of the spaghetti-like networks and along the fiber axis of the carbon nanofibers. Thus, the carbon nanofibers and the silica matrix are interlocked, resulting in a strong attachment of the silica matrix to the carbon nanofibers.

Stability Tests

The stabilizing effect of silica/carbon nanofiber architecture to the enzyme AChE was examined by measuring the sensitivity of the corresponding biosensor under continuous polarization over time. It was found that successive additions of acetylthiocholine lead to an increase of the anodic current, which is attributed to the oxidation of the enzyme's hydrolysis product thiocholine on the surface of the electrode. Thus the sensitivity of the biosensor is directly related to the enzyme activity, allowing the continuous monitoring of enzyme activity. The initial sensitivity of the biosensor comprising the composite silica/CNF/PLL/AChE is calculated to be 7.8 μA/mM. The response of biosensor is linear at acetylthiocholine concentrations from 0.04 mM to 0.3 mM. The response time of the biosensor is between 2 to 4 minutes and the sensor-to-sensor reproducibility is less than 10% RSD (n=3).

As shown in FIG. 3, the biosensor has a remaining activity of 100% under continuous polarization for 13 days at 25° C., biased at +300 mV vs. Ag/AgCl. The initial increase of the biosensor sensitivity is a well-known phenomenon in biosensor systems, attributed to changes of the enzyme's three-dimensional structure inside the immobilization matrix upon rehydration. Of considerable interest is the fact that the biosensor presented a remaining activity of 70% after 3.5 months of continuous polarization, while the free enzyme and the enzyme immobilized on carbon nanofibers (CNF/AChE) showed a considerable decrease of their activity to 50% after 4 and 25 days respectively (data not shown). It is thus evident that the silica/nanofiber architecture provides an environment within which relatively unstable enzymes are highly stabilized.

The free enzyme and the nanostructured composites were also examined for the stability of the enzyme activity under elevated temperatures (50° C.). FIG. 4 shows the stability of the free enzyme, the enzyme immobilized on oxidized carbon nanofibers and the enzyme in the composite material silica/CNF/PLL/AChE, as calculated by the residual activity as a function of incubation time. The stability is expressed as the time at which the enzymatic activity is reduced to 50% ($t_{50}$) compared to the initial activity. The $t_{50}$ of the free enzyme is measured to be only 4 min, while the immobilization of the enzyme on the oxidized carbon nanofibers provides a 20 fold increase in the stabilization as the $t_{50}$ increases to about 80 min. If the carbon nanofibers with the immobilized AChE thereon are encapsulated by means of a biomimetically synthesized silica matrix, then the $t_{50}$ of the system increases to 150 min. It is thus evident that enzyme immobilization on oxidized carbon nanofibers with subsequent silica precipitation provides superior enzyme stabilization against thermal shock and protein denaturation.

Finally the stability of the free and immobilized enzyme against external proteolysis was investigated. The resistance to proteolysis is a direct proof of the physical protection provided by the architecture of the nanostructured composite of the present invention. Since proteases can be found in virtually any non sterile solution, their effect on the biosensor element stability is a very important study needed to be performed in order to prove the ability of the system to be applied to continuous analysis of real samples. As shown in FIG. 5 the free enzyme loses its activity completely after only 1 h in protease (pronase) solution, while the enzyme immobilized onto the oxidized carbon nanofibers retains 37% of its initial activity after 2 h in the same solution. On the other hand, when the AChE enzyme is additionally protected by the silica matrix, its activity is virtually unaffected even after 12 hours of exposure to the protease.

According to the results shown in FIGS. 3 to 5, immobilization on a nanostructured matrix of oxidized (activated) carbon nanofibers provides a stabilization which is effective even with an inherently unstable enzyme like AChE. The presence of a biomimetically synthesized silica matrix further increases the stability of the enzyme. This result might be attributed to a synergy effect of both nanostructured matrix phases, i.e. the oxidized carbon nanofibers and the biomimetically synthesized silica matrix.

Stability Test of a Glucose Sensor

In the same manner as described above for the nanostructured composite silica/CNF/PLL/AChE a nanostructured composite material comprising glucose oxidase (GOx) immobilized on a matrix of oxidized carbon nanofibers encapsulated in a biomimetically synthesized silica matrix is obtained.

Figure 6:
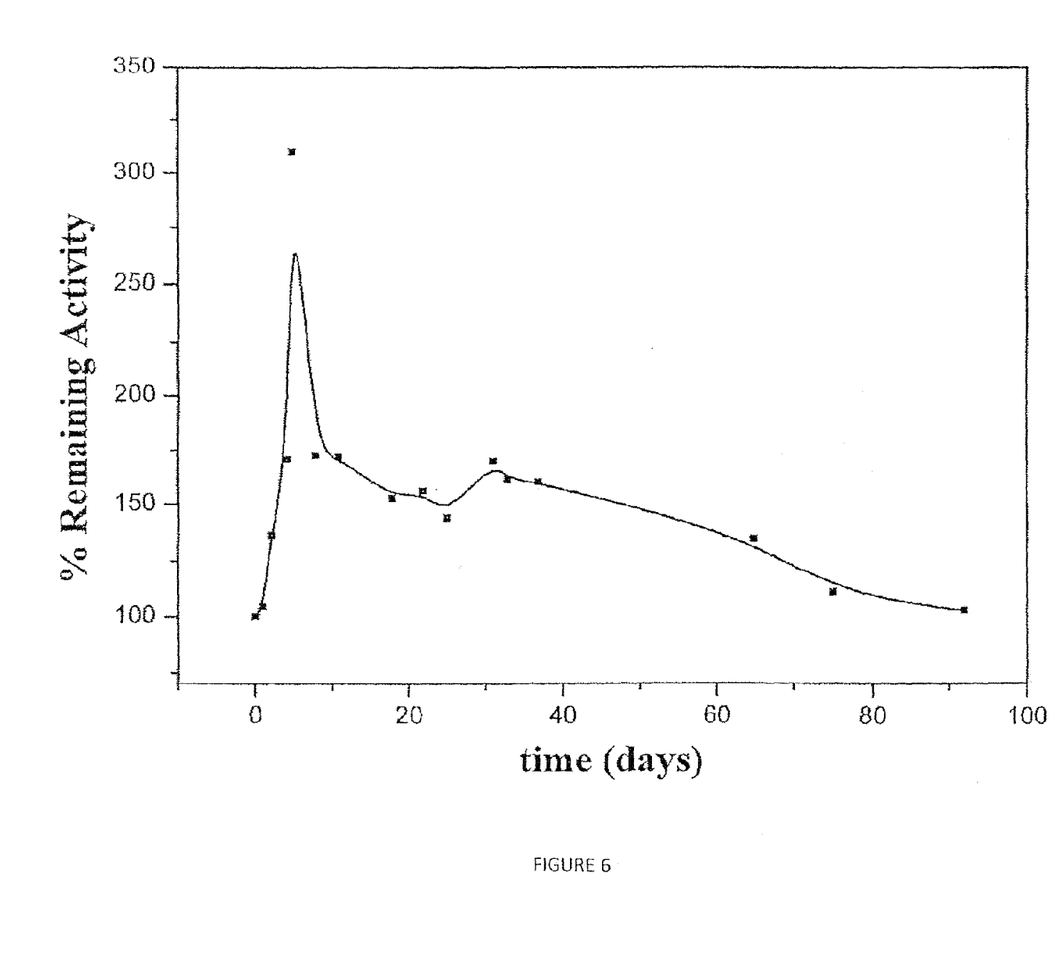
FIG. 6 displays the stability of a nanostructured composite material according to another specific embodiment of the present invention under continuous polarization (+700 mV, 25° C.).

The sensitivity of that biosensor is directly related to the activity of GOx, thus allowing the continuous monitoring of glucose oxidase activity under continuous polarization as described above. After three months an activity of 103% is found, and the experiment is still going on. This result (see FIG. 6 showing a plot of the remaining enzyme activity vs. time) shows that the nanostructured composite is suitable for the application in a biosensor for long-term glucose monitoring as it is necessary in diabetes care.

We claim:

1. Nanostructured composite material, especially for application in biosensors, comprising:
    a silica matrix precipitate on a scaffold comprising a polymer or a peptide, carbon nanofibers; and
    a biochemical receptor immobilized on said carbon nanofibers, wherein said carbon nanofibers are activated.

2. Nanostructured composite material according to claim 1, wherein the biochemical receptor is selected from the group consisting of isolated enzymes, microorganisms, immunosystems, tissues, organelles, whole cells, antibodies, nucleic acids and combinations thereof.

3. Nanostructured composite material according to claim 1, wherein the amount of acidic surface functional groups in the activated carbon nanofibers is at least $6*10^{-5}$ mol/gram.

4. Nanostructured composite material according to claim 1, wherein the scaffold material is selected from the group consisting of poly-L-lysine, polyethylenimine, polyallylamine, cellulose, R5 peptide, poly-L-arginine, poly-L histidine, lysine oligomers, poly(allylamine hydrochloride).

5. Nanostructured composite material according to claim 1, wherein porin molecules are incorporated in the silica matrix.

6. Method for producing a nanostructured composite material according to claim 1, comprising:
    activating carbon nanofibers by treatment with an oxidizing agent;
    adjusting the pH value at the surface of the carbon nanofibers to 7;
    immobilizing a biochemical receptor on the activated carbon nanofibers; and
    optionally, depositing a scaffold comprising a protein or polymer onto the carbon nanofibers and precipitating a silica matrix onto the scaffold.

7. Method according to claim 6, wherein activation of the carbon nanofibers comprises:
    treating the carbon nanofibers with an oxidizing agent selecting from the group consisting of hydrogen peroxide, nitric acid, mixtures of sulfuric acid and nitric acid, oxygen, potassium permanganate ($KMnO_4$) and ruthenium tetroxide ($RuO_4$);
    treating the carbon nanofibers with irradiation;
    supplying thermal energy; or
    a combination thereof.

8. A biosensor comprising a nanostructured composite material according to claim 1.

9. A biosensor according to claim 8, wherein the biosensor is a single needle biosensor for subcutaneous measurement.

10. A biosensor according to claim 8, further comprising a layer comprising a biocompatible material on at least a part of the surface of the biosensor or the multi-biosensor device.

11. A multi-biosensor device comprising a plurality of biosensors, wherein at least one of the biosensors comprises a nanostructured composite material according to claim 1.

12. A multi-biosensor device according to claim 11, wherein means are provided to achieve individual activation of each biosensor.

13. A multi-biosensor device according to claim 12, wherein the biosensors are provided with a covering layer comprising an electrically erodible polymer which is substantially impermeable to fluids, and means are provided to achieve sequential activation of the individual biosensors by electroerosion of said electrically erodible polymer and electronic activation of the uncovered sensor.

14. A multi-biosensor device according to claim 11, wherein the multi-biosensor device can be implanted subcutaneously.

15. A multi-biosensor device according to claim 11, further comprising a layer comprising a biocompatibie material on at least a part of the surface of the biosensor or the multi-biosensor device.

* * * * *